(12) United States Patent
Hancock et al.

(10) Patent No.: US 7,074,960 B2
(45) Date of Patent: Jul. 11, 2006

(54) CATALYSTS

(75) Inventors: Frederick Ernest Hancock, Cleveland (GB); Graham John Hutchings, North Yorkshire (GB); Neil Aubrey Caplan, County Durham (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 10/487,384

(22) PCT Filed: Aug. 5, 2002

(86) PCT No.: PCT/GB02/03609

§ 371 (c)(1),
(2), (4) Date: May 26, 2004

(87) PCT Pub. No.: WO03/018191

PCT Pub. Date: Mar. 6, 2003

(65) Prior Publication Data

US 2004/0204610 A1    Oct. 14, 2004

(30) Foreign Application Priority Data

Aug. 21, 2001  (GB) .................................. 0120256

(51) Int. Cl.
*C07C 45/72* (2006.01)
(52) U.S. Cl. .................................................... 564/271
(58) Field of Classification Search ................. 564/271
See application file for complete search history.

(56) References Cited

U.S. PATENT DOCUMENTS 5,852,205 A * 12/1998 Bethell et al. .............. 548/965

OTHER PUBLICATIONS

Tschaen et al., Stereochemical studies of thermal intermolecular and intramolecular N-sulfonylimine ene reactions, J. Org. Chem.; 1984; 49(26); 5058-5064.*

Keiji Maruoka et al., "Asymmetric Ene Reaction Catalyzed by Chiral Organoaluminum Reagent," *Tetrahedron Letters*, vol. 29, No. 32, 1998, pp. 3967-3970.

Koichi Mikami et al., "Catalytic Asymmetric Glyoxylate-Ene Reaction: A Practical Access to α-Hydroxy Esters in High Enantiomeric Purities," *J. Am. Chem. Soc.*, vol. 12, No. 10, 1990, pp. 3949-3954.

Koichi Mikami, "Asymmetric catalysis of carbonyl-ene reactions and related carbon-carbon bond forming reactions," *Pure & Appl. Chem.*, vol. 68, No. 3, 1996, pp. 639-644.

Yong Gao et al., "Stereoselective Synthesis of *meso*-2,6-Diaminopimelic Acid and Its Selectively Protected Derivatives," *J. Org. Chem.*, vol. 63, No. 7, 1998, pp. 2133-2143.

David A. Evans et al., "$C_2$-Symmetric Copper(II) Complexes as Chiral Lewis Acids. Catalytic Enantioselective Carbonyl-Ene Reactions with Glyoxylate and Pyruvate Esters," *J. Am. Chem. Soc.*, vol. 122, No. 33, 2000, pp. 7936-7943.

William J. Drury, III et al., "A Novel Synthesis of α-Imino Esters," *J. Sam. Chem. Soc.*, vol. 120, No. 42, 1998, pp. 11006-11007.

David A. Evans et al., "Bis(oxazoline)-Copper Complexes as Chiral Catalysts for the Enantioselective Aziridination of Olefins," *J. Am. Chem. Soc.*, vol. 115, No. 12, 1993, pp. 5328-5329.

James K. Whitesell et al., Asymmetric Induction in the Ene Reaction of Glyoxylate Esters of 8 Phenylmenthol, *Tetrahedron*, vol. 42, No. 11, 1986, pp. 2993 to 3001.

International Search Report dated Dec. 5, 2002, from International Application No. PCT/GB02/03609.

* cited by examiner

*Primary Examiner*—Johann Richter
*Assistant Examiner*—Chukwuma Nwaonicha
(74) *Attorney, Agent, or Firm*—RatnerPrestia

(57) ABSTRACT

A zeolite-immobilized Lewis acid e.g. copper catalyst for performing carbonyl-ene and iminoene reactions is described. The catalyst can readily be separated from the reaction mixture and re-used in further reactions with minimal reduction in activity.

8 Claims, No Drawings

CATALYSTS

This invention relates to heterogeneous catalysts and in particular to the heterogeneous catalysis of carbonyl-ene and imino-ene reactions. The products of such reactions are useful chemical intermediates or reagents for use in the production of fine chemicals or pharmaceutical intermediates.

The carbonyl-ene and imino-ene reactions are recognised as particularly useful tools for synthesising carbon-carbon bonds. In general the reaction is carried out between a carbonyl or an imine compound and an alkene having an allylic (γ) hydrogen. Examples of the reaction are depicted below.

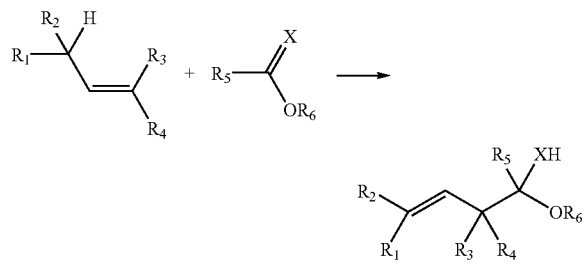

e.g.
$R_1$=H, alkyl ($C_1$–$C_{10}$)
$R_2$=H, alkyl ($C_1$–$C_{10}$)
$R_3$=H, alkyl ($C_1$–$C_{10}$)
$R_4$=H, Ph, alkyl ($C_1$–$C_{10}$)
X=O or $NR_1$
$R_5$=H, alkyl ($C_1$–$C_{10}$), $C(O)_2R_6$
$R_6$=$CH_3$, $C_2H_5$ The reactions thus share the feature of a nucleophilic attack on the carbonyl- or imino-carbon atom by the alkene. The carbonyl-ene reaction has found particular utility for producing hydroxy acids or esters while the use of N-protected imines in the place of the carbonyl compounds gives α-amino acids and esters. In particular carbonyl-ene reactions using α-dicarbonyl compounds, for example α-carbonyl-esters or carboxylic acids, may be used to generate synthetically-useful chiral α-hydroxy carbonyl compounds. Similarly, α-carbonyl imines provide new amino acids. High demand in the pharmaceuticals industry for efficient and economical routes to homochiral α-hydroxy and α-amino carbonyl compounds has driven new developments in catalysis and enantioselectivity.

Methods for performing chiral carbonyl-ene reactions and chiral imino-ene reactions using homogeneous catalysts are known. The first catalytic enantioselective carbonyl-ene reaction was performed using a soluble chiral methyl-aluminium-binaphthol (BINOL) complex, but the scope of this catalyst was limited to pentafluorobenzaldehyde as the carbonyl component (see Yamamoto et al, *Tet. Lett.*, 1988, 29, 3967). Later, the scope of carbonyl substrates was increased by using soluble chiral titanium-BINOL catalysts although here the alkenes were restricted to 1,1-disubstituted alkenes due to the modest Lewis acidity of the titanium catalysts used (see Mikami & Nakai et al, *J. Am. Chem. Soc.*, 1990, 112, 3949; Mikami, *Pure & Appl. Chem.*, 1996, 68 (3), 639).

More recently workers have focussed on more Lewis acidic, cationic bidentate Copper (II) catalysts having chelating bis(oxazoline) ligands (see for example Vederas et al, *J. Org. Chem.*, 1998, 63, 2133; Evans et al, *J. Am. Chem. Soc.*, 1998, 120, 5824; Evans et al, *J. Am. Chem. Soc.*, 2000, 122, 7936). These compounds have been used as homogeneous catalysts for carbonyl-ene, Diels-Alder, aldol, nitro aldol, Michael addition Friedel-Crafts, and amination reactions. Carbonyl-ene reactions were performed in various solvents at 0.2–50 mol % at temperatures from −30 to 40° C. with a range of glyoxylate or pyruvate esters and substituted alkenes to generate chiral α-hydroxy carbonyl compounds in good yield and high enantiomeric excess. In particular these catalysts were found to be useful for the reaction of ethyl glyoxylate and methyl pyruvate with 1-hexene, 1,1- and 1,2-disubstituted alkenes and trisubstituted cyclic alkenes.

In contract, catalytic enantioselective imino-ene reactions appear to have been limited to α-iminoesters (e.g. $EtO_2CC(NTs)H$) and alkenes catalysed by a soluble copper binaphthylphosphino (BINAP) complex [(R)-Tol-BINAP-Cu][$ClO_4$] (see Leckta et al. *J. Am. Chem. Soc.*, 1998, 120, 11006).

Such catalysts and the processes using them remain limited in their economic efficiency because of the inability to readily remove the catalysts from the reaction medium. Costly solvent extraction techniques are used and concern over the environmental burden of the resulting catalyst waste and the general inability to re-use the separated catalyst make it desirable to employ a heterogeneous catalyst.

We have found that particular zeolites, modified with Lewis acidic metals and treated with chelating bis(imine) compounds, e.g. bis(oxazolines), are active heterogeneous catalysts and may be readily removed from the reaction mixture and successfully re-used. In U.S. Pat. No. 5,852, 205, a metal-exchanged acidic zeolitic material, for example copper-exchanged zeolite Y, is described that may be used for the effective heterogeneous catalysis of the reaction between alkenes and nitrene donors to form aziridines. Furthermore, chiral aziridines could be prepared using these catalysts in combination with chiral bis(oxazoline) modifiers (see also P. McMorn et al, *Appl. Cat. A.*, 1999, 182, 85).

We have found surprisingly that the usefulness of certain metal-exchanged zeolitic catalysts described for the aziridination reaction may be extended to the mechanistically distinct carbonyl-ene and imino-ene reactions. However, unlike the aziridination reaction, the carbonyl-ene and imino-ene reactions are very slow in the absence of a chelating bis(imine) compound.

Consequently, the combination of a metal exchanged zeolite and a chiral bis(imine) is able to provide acceptable reaction rates and comparable enantiomeric excesses (e.e's) to the homogeneous copper bis(oxazolinyl) salts previously described but with the added advantage that the catalysts may readily be recovered from the reaction mixture and re-used.

Accordingly the invention provides a process for performing a carbonyl-ene or an imino-ene reaction by reacting a carbonyl compound or an imine compound with an alkene in the presence of a heterogeneous catalyst comprising a zeolitic material exchanged or impregnated with ions of a Lewis acidic metal and treated with a chelating bis(imine) compound.

The zeolite employed will depend on the nature of the reactants and the reaction product. The zeolite is selected from the group of structures with at least 10 ring apertures such as DAC, EPI, EUO, FER, HEU, LAU, MEL, MFI, MFS, MTT, NES, STI, WEI, -PAR and -WEN and structures with 12-ring apertures such as *BEA, BOG, CAN, EMT, FAU, GME, LTL, MAZ, MEI, MOR, MTW, OFF and -RON. Preferably, the zeolite is selected from the group of structures having 12-ring apertures. Full details of these structures may be found in the "*Atlas of Zeolite Structure Types*" (W. M. Meier, D. H. Olson and C. Baerlocher, 4th Edition, Elsevier, 1996). The most preferred zeolite structure is FAU. It will be readily understood by those skilled in the art that FAU covers a range of framework compositions (i.e. silica: alumina ratios). While all such compositions are useful, preferably the FAU has a silica:alumina ratio of 5:1 and more preferably 12:1, and although higher silica:alumina ratios can be used, the reduction in exchangeable sites (associated with aluminium in the framework) means that very high silica:alumina ratios are less preferred. The FAU zeolite structure corresponds to zeolite X and zeolite Y. The preferred zeolite is zeolite Y.

The catalyst of the present invention is a zeolite in which at least some of the exchangeable cation sites are occupied by Lewis acidic metal ions. Preferably, between 1 and 100% of the exchange sites occupied by Lewis acidic metal ions, preferably 10–80%, most preferably 25–75%. The Lewis acidic metal ions comprise at least one metal selected from Groups VB, VIB, VIII, IB, IIB or IIIA of the Periodic Table (as set out in the UK Abridgements of Patent Specifications for the Series 1525001 to 1537580). Preferred metals are V, Cr, Cu, Zn or Al. The preferred metal is Cu (copper) and the preferred catalyst is copper-exchanged zeolite Y.

The exchanged catalyst may contain between 0.1 and 15% by weight, preferably 0.5 to 7% by weight and most preferably 1 to 5% by weight of Lewis acidic metal.

The catalyst may be made directly from the zeolite using wet impregnation ion exchange techniques in the pH range 4 to 8 and preferably 5 to 7.5. Alternatively, dry impregnation of metal ions into the zeolite may be used, for example by dry-blending followed by a heat treatment. It shall be understood by those skilled in the art that a portion of the metal ions will be exchanged following treatment and that a portion will remain un-exchanged but trapped within the zeolite cage structure. Where metal ions are trapped within the zeolite cage structure, the zeolite may be described as impregnated. Both ion-exchanged and impregnated materials are effective in the process of the present invention. It is preferable to maximise ion-exchange and minimise impregnation when preparing catalysts that may be subjected to recovery and re-use to minimise leaching of the metal from the zeolite. The exchange/impregnation process may be carried out once, or repeated to obtain the desired metal loading. In wet impregnation ion exchange, sources of the metal are typically aqueous solutions of salts such as the nitrate, sulphate or carboxylates such as the acetate, oxalate or citrate. For example, for copper, suitable salts are copper nitrate, copper oxalate and copper acetate. The exchanged zeolite is then separated by filtration or by centrifuging, and may be washed to remove any unbound metal ions, and dried. Before use, the exchanged zeolite may, if desired, be calcined to remove counter ions, e.g. acetate, not removed by washing. Herein, drying refers to a process where absorbed solvent, e.g. water, is driven off by heating at temperatures up to about 170° C., and calcining refers to a process where organic residues on the catalyst are destroyed by heating to temperatures above their decomposition temperature, for example 350–600° C.

The catalyst may be in any form readily used for the process, i.e. as a powder, granules, pellets or extrudates. These may be prepared by techniques known to those skilled in the art, including pelletising, extruding and spray-drying. The exchange/impregnation process may be performed on pellets or granules before, during or after forming using such techniques.

To provide a suitably active catalyst, the metal-exchanged zeolitic material is subjected to a reaction with a chelating bis(imine). By the term "chelating" we mean a compound capable of forming at least two bonds with a metal atom. Suitable chelating bis imines are compounds of formula (I) or formula (II);

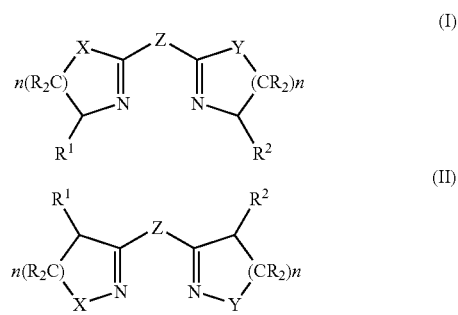

in which R, $R^1$ and $R^2$ are independently hydrogen, alkyl (branched or linear C1–C10), cycloalkyl, aryl or benzyl which may be substituted or unsubstituted; substituting groups being selected from a list comprising halogen, hydroxyl, carboxyl, amide, silyl and aryl; n is independently 1 or 2; X and Y are independently O, S, $CR_2$ or NR' (in which R' may be hydrogen, alkyl (branched or linear C1–C10), or an electron withdrawing group, e.g. $CO_2Et$); and Z is a linking group that links the carbons of the imine groups via between 0 and 3 linking atoms. For example Z may be of formula NR" or $CR"_2$ in which R" is independently hydrogen or alkyl, (branched or linear C1–C10) through which the imine groups are linked via the N and C atoms respectively, or pyridine, linked via the carbon atoms adjacent to the nitrogen atom of the pyridine ring. Furthermore, R, R', R", $R^1$ and $R^2$ may be linked so as to form at least one ring in the bis(imine) structure. En-amine compounds that are capable of forming chelating bis(imine) compounds according to formula (I) or formula (II) are also necessarily included in the present invention.

Preferably the bis(imine) is chiral and possesses $C_2$-symmetry. Accordingly the bis(imine) may possess an axis of symmetry through Z and consequently have $R^1$ and $R^2$ the same; n the same for both imine rings and the same X and Y groups. Such bis(imines) include but are not restricted to the following wherein $R^1$ and $R^2$ are as hereinbefore defined and where Me=$CH_3$, Et=$C_2H_5$ and Ph=$C_6H_5$;

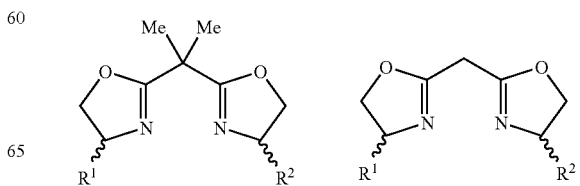

-continued

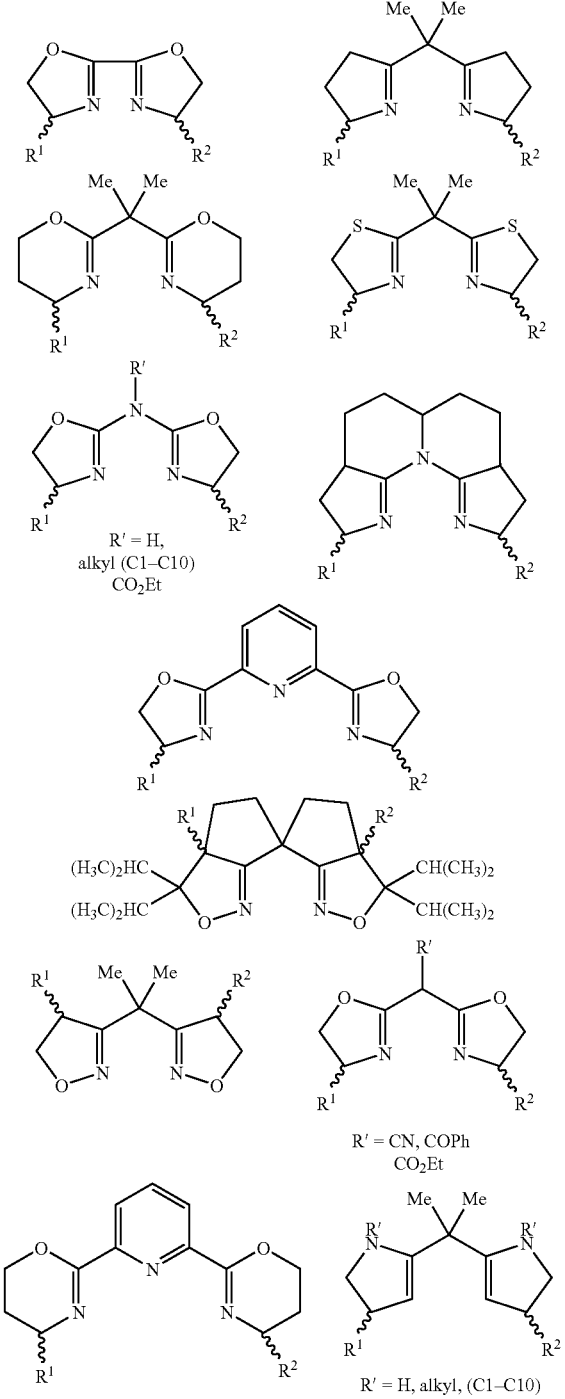

R is preferably hydrogen. $R^1$ and $R^2$ are preferably tert-butyl ($C(CH_3)_3$), iso-propyl ($CH(CH_3)_2$), phenyl ($C_6H_5$) or benzyl ($CH_2C_6H_5$); n is 1; X and Y are O and Z is $CH_2$, $C(CH_3)_2$, $NCH_3$ or 1,5-$C_5H_5N$. Accordingly, particularly preferred chelating bis(imines) include chiral disubstituted bis(oxazolines), disubstituted iso-oxazolines, symmetrical semicorrins and aza-semicorrins. Suitable chiral chelating bis(oxazolines) include (S,S)-bis(tert-butyloxazolines), (R,R)-bis(phenyloxazolines), (S,S)-bis(phenyloxazolines) and (R,R)-bis(benzyloxazolines). For example, with Z=$C(CH_3)_2$, and $R^1$ & $R^2$=tert-butyl, the bis(imine) compound is 2,2'-isopropylidenebis[4(S)-4-tert-butyl-2-oxazoline]; with Z=$CH_2$, the bis(imine) is 2,2'-methylenebis[4(S)-4-tert-butyl-2-oxazoline]. These chiral chelating bis(imine) compounds have $R^1$ and $R^2$ bonded to chiral centres. The designations "(S,S)", and "(R,R)" describe the chiral configuration of the $R^1$ and $R^2$ groups within the bis(imine) structure. An (R,R)-bis(imine) may, depending upon the structure of the carbonyl compound or alkene, provide a reaction product bearing a chiral hydroxyl group in an enantiomeric excess of either the (R) or (S) configuration. Furthermore, the nature of the alkene reacted with the carbonyl compound or imine compound may provide for reaction diastereoselectivity which may be influenced by the choice of chelating bis(imine) compound used. For example, 1,2-disubstituted alkenes such as cyclohexene or 2-methylhept-2-ene provide the potential for reaction diastereoselectivity which may be influenced by the choice of chelating bis(imine) compound used.

In the present invention the metal-exchanged zeolite is treated with the chelating bis(imine) compound before contact with the alkene and carbonyl compound or imine compound. In the absence of the chelating bis(imine) compound treatment of the zeolite, the reaction rates can be extremely poor, e.g. <5% conversion after 14 days at room temperature using unmodified copper-exchanged zeolite Y. However, we have found that the amount of chelating bis(imine), for example bis(oxazoline), required may be considerably less than with homogeneous catalysis. Thus whereas it is usual in homogeneous catalysis to use one or more moles of chelating bis(oxazoline) per gram atom of the catalytic metal, in the present invention if more than one mole of chelating bis(oxazoline) is used per gram atom of catalytic metal, the yields of desired product may be decreased, possibly as a result of the excess of bis(oxazoline) blocking the zeolite supercage structure. We prefer to employ not more than one equivalent of chelating bis(imine) per Lewis acidic metal ion within the zeolite structure and most preferably between 0.40 and 0.75 molar equivalents of chelating bis(imine) per Lewis acidic metal ion within the zeolite structure.

The treatment of the metal-exchanged zeolite with chelating bis(imine) compound to form the active catalyst may conveniently be performed separately from the process of the present invention or immediately before use. The generation of the active catalyst may be carried out in one of the reactants, preferably the alkene, or a suitable solvent. For example, where the alkene is liquid under the reaction conditions, it may be possible to disperse the metal-exchanged zeolite within it and add the chelating bis(imine) compound to it in order to generate the active catalyst before adding the carbonyl compound or imine compound. However, it may be more convenient to use a suitable solvent. In a typical method for generating the active catalyst, metal-exchanged zeolite is dispersed in a solvent and the chelating bis(imine) compound added and stirred for sufficient time, e.g. 3 hours, for the bis(imine) compound to complex with the Lewis acidic metal.

Regardless of whether or not a solvent was used in the process of generating the active catalyst from metal-exchanged zeolite and chelating bis(imine) compound, it may be possible to perform the reaction between the alkene and carbonyl compound or imine compound in the absence of a solvent if the reactants are liquids. Hence in a first embodiment the process is simply performed by adding the bis(imine)-treated metal-exchanged zeolite to the liquid mixture of reactants and stirring for sufficient time until the reaction is complete, separating the catalyst by filtration and purifying the crude product using, e.g. flash column chromatography.

However the use of solvents may be preferable, for example where the reactants are viscous liquids or solids. Hence in a second embodiment, reactants and the bis (imine)-treated metal-exchanged zeolite are combined in a suitable solvent. After sufficient time for the reaction to occur, the catalyst is removed by filtration and the crude product purified using, e.g. flash column chromatography.

The compounds prepared by the process of the present invention are amino- or hydroxyl-containing compounds formed by the reaction of a carbonyl compound or in imine compounds with an alkene. The carbonyl compounds and imine compounds share the feature of an electropositive carbon (bonded to the oxygen or nitrogen atoms respectively) susceptible to reaction with an alkene, which may accelerated in the presence of a Lewis Acid catalyst. The carbonyl compound and imine compound may therefore be described by formula (III)

(III)

in which X is O or $NR^3$, $R^3$ may be hydrogen, alkyl (C1–C10), aryl or a removable leaving group, e.g. tosyl (Ts), $R^4$ may be hydrogen or substituted or unsubstituted alkyl (C1–C10), cycloalkyl, heteroalkyl, aryl or alkoxyl (i.e. $OR^3$) and $R^5$ may be substituted or unsubstituted alkyl (C1–C10), cycloalkyl, heteroalkyl, aryl, carbonyl (i.e. $C(O)R^3$) or carboxyl (i.e. $C(O)OR^3$). Substituting groups may be alkyl, aryl, silyl, heteroaryl or phosphonate.

Preferably the resulting amino- or hydroxyl-containing compound possesses a chiral centre. Thus preferably $R^4$ and $R^5$ are not the same.

The carbonyl-ene and imino-ene reactions utilising homogeneous catalysts reported previously have used carbonyl compounds and imine compounds that have an electron-withdrawing group, usually a carbonyl or carboxyl group, adjacent to the carbonyl or imine carbon atom to enhance its reactivity. We have found surprisingly that using the process of the present invention such electron withdrawing groups may not be necessary. For example we have found that alkylimine compounds, e.g. isovaler-N-benzyl-imine may usefully be reacted with α-methylstyrene in the presence of the zeolite-immobilised catalysts. Furthermore we have found that 1,2-trisubstituted alkenes, e.g. 2-methylhept-2-ene that are not reactive with α-dicarbonyl compounds using homogeneous catalysts react under relatively mild conditions using the process of the present invention.

Preferably the carbonyl compound is a α-dicarbonyl compound. Suitable α-dicarbonyl compounds include glyoxylate esters, e.g. ethyl glyoxylate and pyruvate esters, e.g. methyl pyruvate. (Ethyl glyoxylate exists in a polymeric form under normal conditions. It may be used in the process of the present invention either in this polymeric form but is preferably used pre-distilled and/or as a solution in a suitable solvent e.g. toluene). Preferably the imine compound is an α-carbonyl imine, α-carboxyl imine or alkyl imine. Most preferred imine compounds are α-carboxyl imine compounds where $R^4$=carboxyl and $R^5$ is hydrogen (i.e. $R^3O(O)CC(NR^3)H$), e.g. ethyl N-benzhydryliminoethanoate.

The alkenes suitable for use in the process of the present invention include unsubstituted alkenes, e.g. hex-1-ene; unsymmetrical 1,1-disubstituted alkenes, e.g. α-methylstyrene, 2-methyl-1-butene, 2-methyl hept-1-ene and compounds of formula;

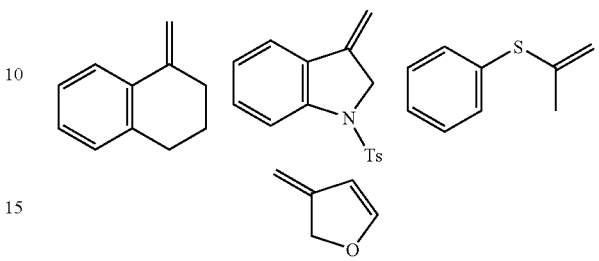

or symmetrical 1,1-disubstituted alkenes, e.g. methylene cyclohexane, methylene cyclopentane and isobutene; functionalised 1,1-disubstituted alkenes, e.g. silyl- and benzyl-protected methallyl and homomethallyl alcohol derivatives; 1,2-disubstituted alkenes, e.g. cyclohexene and even 1,2-trisubstituted alkenes, e.g. 1-methylcyclohexene or 2-methylhept-2-ene.

The molar ratio of carbonyl compound or imine compound to alkene may be 1:1 however an excess of carbonyl compound or imine compound relative to alkene improves the yields of product from the reactions. For example carbonyl or imine to alkene ratios of between 1:1 and 10:1 and preferably 2:1 to 6:1 may be used in the present process. Alternatively an excess of alkene may similarly be used to increase yield and enantioselectivity.

Solvents are preferably used in the process of the present invention. The solvents may be polar or non-polar. Examples include aromatic hydrocarbons such as toluene, xylene or mesitylene, halocarbons such as dichloromethane or chloroform, ethers such as diethyl ether or tetrahydrofuran. Preferably, the solvent is a polar solvent and most preferably, the solvent is dichloromethane. Strongly co-ordinating solvents such as acetonitrile that may interfere with chelation of the bis(imine) with the immobilised Lewis Acid are less preferred.

The reaction conditions employed in the process depend upon the nature, i.e. boiling point or stability, of the solvent and reactants or products. Reaction temperatures are generally in the range −30° C. to +80° C. For example, the formation of α-hydroxy and α-amino carbonyl compounds the temperature is preferably in the range between 0 and 40° C. The process may be effected at any suitable pressure, e.g. atmospheric, although where the alkene or the reaction product is volatile or gaseous at the reaction temperature, the reaction pressure should be sufficient to maintain them in the liquid state e.g. in solution. The process of the present invention may be effected batch-wise or continuously. In a batch reaction, to obtain a useful reaction rate, the amount of catalyst employed is preferably such that there are about 0.01 to 0.5 molar equivalents and more preferably 0.02 to 0.25 molar equivalents of Lewis acidic metal per mole of alkene.

An advantage of the catalysts of the present invention is that they may readily be separated from the reaction mixture and, if desired, re-used for subsequent reactions. The catalysts may be separated by known methods such as filtration or centrifugation. To remove undesirable residues of the reaction mixture from the catalyst, it may be advantageous to wash the catalyst using a suitable solvent for said undesirable residues and dry prior to re-use. Suitable solvents include aliphatic hydrocarbons such as hexane or heptane, aromatic hydrocarbons such as toluene, xylene or mesitylene, halocarbons such as dichloromethane or chloroform, ethers such as diethyl ether and esters such as ethyl acetate. The separated catalyst is preferably washed with ethyl acetate and dried under vacuum to remove traces of solvent and/or any traces of the reaction mixture prior to re-use. Preferable drying temperatures are in the range 20 to 160° C. under vacuum for between 1 and 24 hours. Additionally, if it is desired to change the bis(imine) compound on the metal-exchanged zeolite, the catalyst may be calcined at temperatures of, e.g. 550° C. for e.g. 6 hours to completely destroy any organic residues. As a consequence, the calcined metal-exchanged zeolite will require treatment with a chelating bis(imine) compound prior to re-use.

The invention is illustrated by the following examples.

EXAMPLE 1

Preparation of a Copper Exchanged Zeolite Y

A 150 ml solution of copper (II) acetate (7.85 g, 39.3 mmol) was prepared using de-ionised water and buffered to approximately pH 6.5 using aqueous ammonia solution (35% wt). A commercially available Zeolite HY (50 g) was then added to the solution and the resulting suspension stirred at room temperature (ca 20° C.). The pH was monitored after 5 minutes and at 1, 2 and 5 hours and adjusted back to 6.5 where necessary with aqueous ammonia solution. The suspension was stirred for 16 hours then the exchanged zeolite was recovered by filtration and washed with de-ionised water. The exchanged zeolite was then dried at 110° C. followed by calcination at 550° C. for 6 hours. The copper loading of the resultant powder was measured by Inductively Coupled Plasma Atomic Absorption Spectroscopy (ICPAAS) at 3.1% by weight.

EXAMPLE 2

Heterogeneously Catalysed Glyoxylate-ene Reaction

Solvent-damp copper-exchanged zeolite Y (0.360 g, 85%, 0.15 mmol Cu) as prepared in Example 1 was placed in a Schlenk flask and dried under a high vacuum at 150° C. for 2 hours. The flask was allowed to cool under nitrogen to room temperature (ca 20° C.). To the cool solid were added dichloromethane (DCM) (5.0 ml) and chelating bis(imine) compound [(R,R)-PhBox (1)] (0.025 g, 0.075 mmol) by syringe. The suspension was stirred for 3 hours at room temperature (ca 20° C.) and then α-methylstyrene (194 µl, 0.177 g, 1.49 mmol) and ethyl glyoxylate (1.02 g, 80% solution in toluene, 7.47 mmol) were added by syringe. The reaction mixture was stirred at room temperature and followed periodically by thin-layer-chromatography (using 30:70 diethyletherhexane). When the reaction was deemed complete, the catalyst was separated by filtration. The crude product was purified by flash column chromatography to yield the product as a mobile liquid. The enantiomeric excess was determined using standard chiral HPLC techniques (see procedures within D. A. Evans et al, *J. Am. Chem. Soc.,* 2000, 122, 7936).

The experiment was repeated using a range of different alkene substrates and bis(oxazoline) compounds (1–3 below). The results are depicted in Table 1.

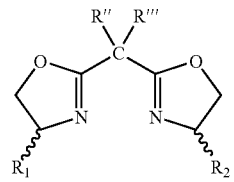

(1) R'' = CH$_3$; R$_1$ = R$_2$ = C$_6$H$_5$
(2) R'' = CH$_3$; R$_1$ = R$_2$ = C(CH$_3$)$_3$
(3) R'' = H; R$_1$ = R$_2$ = C(CH$_3$)$_3$

TABLE 1

Examples: Ethyl Glyoxylate - Ene Reaction

| Example | Bis(imine) | Alkene | Product | Time (hrs) | Yield (%) | Ee (%) |
|---|---|---|---|---|---|---|
| 2a | (S,S)-(1) | α-Methylstyrene | | 20 | 85 | 77 |
| 2b | (S,S)-(1) | Methylene cyclohexane | | 100 | 65 | 94 |
| 2c | (S,S)-(1) | Methylene cyclopentane | | 100 | 71 | 93 |

TABLE 1-continued

Examples: Ethyl Glyoxylate - Ene Reaction

| Example | Bis(imine) | Alkene | Product | Time (hrs) | Yield (%) | Ee (%) |
|---|---|---|---|---|---|---|
| 2d | (R,R)-(1) | 2-methylheptene | [structure: C₄H₉ substituted methylene with CH₂-C(OH)(H)-C(O)OEt] | 150 | 69 | 72 |
| 2e | (R,R)-(1) | 2-Methylhept-2-ene | [structure: major product with isopropenyl group and butyl chain, CH₂-C(OH)(H)-C(O)OEt]  major  [structure: minor product with trisubstituted alkene, C(CH₃)₂-C(OH)(H)-C(O)OEt] minor | 150 | 23 | 77 |
| 2f | (S,S)-(2) | α-Methylstyrene | [structure: phenyl-C(=CH₂)-CH₂-C(OH)(H)-C(O)OEt] | 12 | 87 | 93 |
| 2g | (S,S)-(3) | α-Methylstyrene | [structure: phenyl-C(=CH₂)-CH₂-C(OH)(H)-C(O)OEt] | 12 | 91 | 85 |

(R,R)-(1) with cyclohexene produced a product with a endo:exo diastereoselectivity of 5.1:1 (i.e. ca. 85:15). Similarly, (R,R)-(1) with 2-methylhept-2-ene produced a major and minor product in a molar ratio of 3.2:1 (i.e. ca 76:24). The anti:syn diastereoselectivity of the major product was 5:1 (i.e ca. 83:17). The results demonstrate that the heterogeneous copper catalysts of the present invention are active for the carbonyl-ene reaction across a range of alkene substrates, including the 1,2-trisubstituted 2-methylhept-2-ene, which according to Evans does not respond a homogeneous copper catalyst (see Evans et al, *J. Am. Chem. Soc*, 2000, 122, page 7938).

EXAMPLE 3

Heterogeneously Catalysed Pyruvate-ene Reaction

The method of Example 2 was repeated using dried catalyst (0.360 g, 85%, 0.15 mmol Cu) for the reaction, in DCM, of (α-methystyrene (0.177 g, 1.49 mmol) with methyl pyruvate (0.85 g, 90%, 7.47 mmol) in place of the ethyl glyoxylate. (R,R)-(1) (0.025 g, 0.075 mmol) was added to the reaction mixture prior to the alkene and methyl pyruvate. The results are depicted in Table 2.

TABLE 2

Example Methyl pyruvate - Ene Reaction

| Example | Bis(imine) | Alkene | Product | Time (hrs) | Yield (%) | Ee (%) |
|---|---|---|---|---|---|---|
| 3a | (R,R)-(1) | α-Methylstyrene | [structure: phenyl-C(=CH₂)-CH₂-C(CH₃)(OH)-C(O)OEt] | 20 | 66 | 74 |

The catalyst was recovered by filtration from the reaction mixture. The crude product was diluted with DCM (20 ml) and washed with cold water (25 ml). The organic phase was separated, dried over anhydrous magnesium sulphate and concentrated under vacuo. The aqueous phase from the crude product washing step was analysed by Inductively Coupled Plasma Atomic Absorption Spectroscopy (IC-PAAS) to determine the amount of leached copper.

The whole experiment was then repeated a further two times (using fresh catalyst for the reaction of α-methyl styrene and methyl-pyruvate). The results are depicted in Table 3.

TABLE 3

Copper Leaching Methyl pyruvate - Ene Reactions

| Example | Copper Added (mg) | Copper Leached (mg) | % Copper Leached |
|---|---|---|---|
| 3a | 9.44 | 0.244 | 2.6 |
| 3b | 8.92 | 0.113 | 1.3 |
| 3c | 11.94 | 0.121 | 1.0 |

The results show that very little copper is lost from the catalyst under normal reaction conditions.

EXAMPLE 4

Heterogeneously Catalysed Imino-ene Reaction

The method of Example 2 was repeated using dried catalyst (0.423 g, 85%, 0.17 mmol Cu) for the reaction, in DCM, of α-methystyrene (0.803 g, 6.79 mmol) with ethyl-N-benzhydrylimonoethanoate (4a) (0.453 g, 1.20 mmol) or isovaler-N-benzyl-imine (4b) (0.219 g, 2.55 mmol) in place of the ethyl glyoxylate. (S,S)-(2) (0.025 g, 0.075 mmol) was added to the reaction mixture prior to the alkene and imine compound. The results are depicted in Table 4.

The results demonstrate that both α-carboxyl and alkyl imine compounds react with alkenes in the presence of the immobilised Lewis Acid

EXAMPLE 5

Recyclability of Heterogeneous Catalysts

A large-scale ethyl glyoxylate-α-methylstyrene experiment (Example 5a) was performed according to the method of Example 2 to provide, following separation, a 'used-catalyst', which was divided into three portions. Each portion was then treated in a different way before re-use in subsequent smaller-scale ethyl glyoxylate and methyl-pyruvate reactions.

(i) Example 5a

Ethyl glyoxylate (4.08 g, 29.88 mmol) was reacted at room temperature (ca 20° C.) with α-methylstyrene 0.708 g, 776 µl, 5.94 mmol) for 20 hours in DCM (20 ml) using as catalyst a copper-exchanged zeolite Y (1.44 g, 0.60 mmol Cu) pre-treated with (R,R)-(1) (0.10 g, 0.40 mmol). The catalyst was recovered by filtration and the crude product purified by flash column chromatography.

(ii) Example 5b–5f

At an approximate ¼ scale to Run 1, ethyl glyoxylate or methyl pyruvate were reacted at room temperature (ca 20° C.) for 20 hours with α-methylstyrene using a portion of recovered catalyst from Run 1, pre-treated according to one of the following methods;

(i) Vacuum oven drying only (60° C., 12 hrs/150° C., 3 hrs)

(ii) ethylacetate wash (5×5 ml) before drying as above,— repeated twice more, or

TABLE 4

Example Imino - Ene Reaction

| Example | Bis(imine) | Imine Compound | Product | Time (hrs) | Yield (%) | Ee (%) |
|---|---|---|---|---|---|---|
| 4a | (S,S)-(2) | EtO₂C–CH=N–CH(Ph)Ph | (structure) | 10 | 87 | 90 |
| 4b | (S,S)-(2) | isovaler-N-benzyl-imine | (structure) | 5 | 83 | 92 |

(iii) washed, dried and then calcined at 550° C., 6 hrs, then re-treated with (R,R)-(1) (0.025 g, 0.075 mmol).

The results are depicted in Table 5.

TABLE 5

Recyclability of Heterogeneous Catalysts

| Example | Re-use | Pre-treatment | Carbonyl Compound | Yield (%) | Ee (%) |
|---------|--------|---------------|-------------------|-----------|--------|
| 5a | — | — | Ethyl-glyoxylate | 66 | 80 |
| 5b | 2nd use | (i) | Ethyl-glyoxylate | 85 | 65 |
| 5c | 2nd use | (ii) | Methyl-pyruvate | 85 | 83 |
| 5d | 3rd use | (ii) | Methyl-pyruvate | 91 | 89 |
| 5e | 4th use | (ii) | Ethyl-glyoxylate | 69 | 82 |
| 5f | 2nd use | (iii) | Methyl pyruvate | 79 | 90 |

These results demonstrate that the catalyst may be suitably active for performing different carbonyl-ene reactions following separation from the reaction mixture and subjected to different treatments.

The invention claimed is:

1. A process for performing an imino-ene reaction, by reacting a

(III)

compound of formula (III)
in which X is $NR^3$, $R^3$ is hydrogen, alkyl (C1–C10), aryl or a removable leaving group, $R^4$ is hydrogen or substituted or unsubstituted alkyl (C1–C10), cycloalkyl, heteroalkyl, aryl or alkoxyl and $R^5$ is substituted or unsubstituted alkyl (C1–C10), cycloalkyl, heteroalkyl, aryl, carbonyl or carboxyl with an alkene in the presence of a heterogeneous catalyst comprising zeolite Y exchanged or impregnated with copper ions and treated with a 4,4'-disubstituted bis(oxazoline).

2. A process according to claim 1 wherein the catalyst contains 0.1 to 15% by weight of copper.

3. A process according to claim 1 wherein between 0.40 and 0.75 molar equivalents of 4,4'-disubstituted bis(oxazoline) are present relative to the copper ions.

4. A process according to claim 1 wherein the compound (III) is an α-dicarbonyl compound.

5. A process according to claim 1 wherein the compound (III) is selected from the group consisting of α-carbonyl imines, α-carboxyl imines, and alkyl imines.

6. A process according to claim 1 wherein the alkene is selected from the group consisting of unsubstituted alkenes, unsymmetrical 1,1-disubstituted alkenes, symmetrical 1,1-disubstituted alkenes, functionalised 1,1-disubstituted alkenes, 1,2-disubstituted alkenes, and 1,2-trisubstituted alkenes.

7. A process according to claim 1 wherein the amount of catalyst used provides between 0.01 and 0.5 moles of copper per mole of alkene.

8. A process according to claim 1 wherein upon completion of the reaction, the catalyst is separated from the reaction mixture and re-used.

* * * * *

UNITED STATES PATENT AND TRADEMARK OFFICE
CERTIFICATE OF CORRECTION

PATENT NO. : 7,074,960 B2 Page 1 of 1
APPLICATION NO. : 10/487384
DATED : July 11, 2006
INVENTOR(S) : Hancock et al.

It is certified that error appears in the above-identified patent and that said Letters Patent is hereby corrected as shown below:

At column 16, delete claim 4.

Signed and Sealed this

Seventh Day of November, 2006

JON W. DUDAS
*Director of the United States Patent and Trademark Office*